United States Patent [19]

Arimura

[11] Patent Number: 5,763,402
[45] Date of Patent: Jun. 9, 1998

[54] PROMOTION OR INHIBITION OF SPERMATOGENESIS

[75] Inventor: Akira Arimura, New Orleans, La.

[73] Assignee: The Administrators Of The Tulane Educational Fund, New Orleans, La.

[21] Appl. No.: 687,654

[22] Filed: Jul. 26, 1996

[51] Int. Cl.$^6$ .................... A61K 38/00; C07K 5/00; C07K 7/00; C07K 17/00
[52] U.S. Cl. .................. 514/12; 514/13; 514/14; 514/15; 514/16; 514/17; 514/18; 514/19; 530/324; 530/325; 530/326; 530/327; 530/328; 530/329; 530/330; 530/331; 530/350
[58] Field of Search ............. 514/12–19; 530/324–331, 530/350

[56] References Cited

U.S. PATENT DOCUMENTS 5,128,242  7/1992  Arimura et al. ................. 435/7.21

OTHER PUBLICATIONS

West et al. J. Endo. vol. 144 p. 215, Feb. 1995.
Shioda et al, Endocrinology vol. 135 p. 818, 1994.
Akira Arimura, "Receptors for Pituitary Adenylate Cyclase–Activating Polypeptide", TEM 3:288–294, 1992.
Arimura et al., "PACAP Functions as a Neutrotrophic Factor", Annals New York Academy of Sciences 228–243, (1992).
Akira Arimura, "Pituitary Adenylate Cyclase Activating Polypeptide (PACAP): Discovery and Current Status of Research", Regulatory Peptides 37:287–303, 1992.
Arimura et al., "Pituitary Adenylate Cyclase Activating Polypeptide (PACAP) and its Receptors: Neuroendocrine and Endocrine Interaction", Frontiers In Neuroendocrinology 16:58–88, 1995.
Arimura et al., "Tissue Distribution of PACAP as Determined by RIA: Highly Abundant in the Rat Brain and Testes", Endocrinology 129:2787–2789, 1991.
Gottschall et al., "Characterization and Distribution of Binding Sites for the Hypothalamic Peptide, Pituitary Adenylate Cyclase–Activating Polypeptide", Endocrinology 127:272–277, 1990.
Heindel et al., "A Novel Hypothalamic Peptide, Pituitary Adenylate Cyclase Activating Peptide, Modulates Sertoli Cell Function in Vitro", Biology of Reproduction 47:800–806, 1992.
Miyata et al., "Isolation of a Neuropeptide Corresponding to the N–Terminal 27 Residues of the Pituitary Adenylate Cyclase Activating . . . ", Biochemical & Biophysical Research Communications 170:643–648, 1990.
Miyata et al., "Isolation of a Novel 38 Residue–Hypothalamic Polypeptide Which Stimulates Adenylate Cyclase In Pituitary Cells", Biochemical and Biophysical Research Communications 164:567–574, 1989.
Shivers et al., "Two High Affinity Binding Sites for Pituitary Adenylate Cyclase–Activating Polypeptide Have Different Tissue Distributions", Endocrinology 128:3055–2065, 1991.

*Primary Examiner*—Sheela Huff
*Attorney, Agent, or Firm*—Fish & Richardson P.C.

[57] ABSTRACT

A method of promoting or inhibiting spermatogenesis, said method comprising administering to a male an effective amount of PACAP, a PACAP agonist, a PACAP antagonist, PC4, a PC4 agonist, or a PC4 antagonist.

12 Claims, No Drawings

PROMOTION OR INHIBITION OF SPERMATOGENESIS

BACKGROUND OF THE INVENTION

Pituitary adenylate cyclase activating polypeptide (PACAP) is a member of the secretin/glucagon/VIP family of peptides. Arimura, A., Regul. Peptides 37:287 (1992). PACAP was originally isolated from ovine hypothalamic tissues. Miyata, et al., Biochem. Biophys. Res. Commun. 164:567 (1989). PACAP exists in two endogenous amidated forms with 38 (PACAP-38) and 27 (PACAP-27) amino acids, but PACAP-38 is the major form in tissues.

Receptors for PACAP have been localized in a wide variety of tissues and cells, including the hypothalamus, pituitary, brain stem, cerebellum, cerebral cortex, lung, liver, human neuroblastoma, and pancreas. FEBS Lett. 262:77 (1990); Regul. Peptides 35:161 (1991); and Regul. Peptides 37:330 (1992). PACAP and its receptors have also been found in the testes. Arimura, et al., Endocrinology 129:2787 (1991) and Shives, et al., Endocrinology 128:3055 (1991). In a preliminary immunochemical study with an antiserum agent, PACAP-like immunoreactivity was observed during specific stages of spermatogenesis. In addition, in situ hybridization experiments detected PACAP mRNA at earlier stages of spermatogenesis. Shioda, et al., Endocrinology 135:818 (1994). However, no one has shown the effect of PACAP on spermatogenesis.

SUMMARY OF THE INVENTION

The present invention relates to the promotion or inhibition of spermatogenesis to promote or inhibit fertility, respectively. In one aspect, the invention features a method of promoting spermatogenesis, the method comprising administering to a male an effective amount of PACAP, a PACAP agonist, PC4, or a PC4 agonist. In another aspect, the invention features a method of inhibiting spermatogenesis, the method comprising administering to a male an effective amount of a PACAP antagonist or a PC4 antagonist.

What is meant by "PACAP" is PACAP-38 or PACAP-27. What is meant by a "PACAP agonist" is a compound (e.g., a peptide fragment or derivative of PACAP or a PACAP peptidomimedic compound) which either (1) binds to a PACAP receptor (e.g., has a binding constant of at least 1M) and promotes spermatogenesis or (2) stimulates the release or formation of endogenous PACAP in the testes (e.g., a PACAP precursor or activators for the transcription, synthesis or processing of PACAP). What is meant by a "PACAP antagonist" is a compound (e.g., a peptide fragment or derivative of PACAP or a PACAP peptidomimedic compound) which either (1) inhibits the biological activity of endogenous PACAP (e.g., prevents endogenous PACAP's activation of a PACAP receptor in the testes) or (2) inhibits the release or formation of endogenous PACAP in the testes. What is meant by "PC4 agonist" is a compound which (1) possesses the same biological activity of PC4 in the testes (e.g., the formation of PACAP from its precursor) or (2) stimulates the release, formation, or activity of PC4. What is meant by "PC4 antagonist" is a compound which will either (1) inhibit the biological activity of PC4 in the testes (e.g., a substrate for PC4 which is not a PACAP precursor) or (2) inhibits the release or formation of PC4. What is meant by "spermatogenesis" is the formation of viable sperm (e.g., capable of fertilization). Note, the term male refers to either human or animal (e.g., a non-human mammal). In other words, both medical and veterinary applications are within the scope of the present invention.

The compounds of the invention (e.g., PACAP, PACAP agonist, PACAP antagonist, PC4, PC4 agonist, or PC4 antagonist) can be administered systemically or locally to the male. Systemic administration can be achieved parenterally (e.g., intravenous injection, subcutaneous injection, or by implantation of a sustained release formulation), orally, by inhalation, or transdermal (e.g., iontophoretic patch). Local administration to a male can be achieved by subcutaneous injection, implantation of a sustained release formulation, or transdermal administration at the scrotum. The dose of the compound used according to the present invention varies depending upon the manner of administration and the condition of the male to be treated, and ultimately will be decided by the attending physician or veterinarian. Such amount of compound as determined by the attending physician or veterinarian to promote or inhibit spermatogenesis is referred hereto as an "effective amount".

While it is possible for the compound to be administered as the pure or substantially pure compound, it may also be presented as a pharmaceutical formulation or preparation. The formulations to be used in the present invention, for both humans and animals, comprise any of the compounds to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, highly oxidative conditions can lead to the formation of cysteine sulfoxide and to the oxidation of tryptophane. Consequently, it is important to carefully select the excipient.

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient(s) with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations) are also well known in the art. See, e.g., U.S. Pat. Nos. 3,773,919 and 4,767,628 and PCT Publication No. WO 94/15587.

The compounds may also be administered with other compounds capable of stimulating or inhibiting spermatogenesis. Examples of spermatogenesis stimulating agents include follicle stimulating hormone (FSH), testosterone, and agonists thereof. Examples of spermatogenesis inhibitory agents include luteinizing hormone-releasing hormone, androgen inhibitors, ethane dimethanesulfonate, and flutamide.

Other features and advantages of the present invention will be apparent from the detailed description of the invention and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

PACAP, PACAP Agonists, and PACAP Antagonists

The chemical structure of PACAP-38 and PACAP-27 are recited in Arimura, et al., Frontiers in Neuroendocrinology 16(1):55 (1995). PACAP may be synthesized by standard peptide chemistry known in the art or by recombinant techniques (see, e.g., European Patent Application No. 420 604 A3). Various analogs (e.g., agonists and antagonists) have been reported in the art. See e.g., Vandermeers, et al., Eur. J. Biochem. 208:815 (1992); Robberecht, et al., Mol. Pharmacology 42:347 (1992), Bitar, et al., Peptides 15(3):461 (1994); Fourlet, et al., Eur. J. Biochem. 195:535 (1991); Robberecht, et al., Eur. J. Biochem. 207:239 (1992); Fishbein, et al., Peptides 15:95 (1994); and European Patent No. 529,487 A3.

The biological activity of other potential PACAP antagonists can be determined by measuring (1) whether the compound prevents PACAP binding to or activation of its receptors (see, e.g., Robberecht, et al., FEBS Lett. 286:133 (1991)) or (2) whether it inhibits the production or release of PACAP (e.g., determined by radioimmunoassay (Arimura, et al., Endocrinology 129:1787 (1991))).

The biological activity of other potential PACAP agonists can be determined by either (1) determining whether the compound binds to PACAP receptors (see, e.g., Gottschall, et al., Endocrinology 127:272 (1990) and European Patent Application No. 529 487 A3) and determining whether the compound stimulates spermatogenesis (see, e.g., Jackson, et al., J. Reprod. Fert. 71:393 (1984) and Sharpe, et al., J. Endocrinol. 117:19 (1988)) or (2) determining whether the compound stimulates the production or release of PACAP.

PC4, PC4 Agonists, and PC4 Antagonists

The chemical structure, isolation, and gene encoding PC4 is recited in the art. Ge, et al., Cell 78:513 (1994); DeSeve, et al., Mol. Endocrinol. 6:1559 (1992); and Nakagawa, et al., J. Biochem. 113:132 (1993). Potential agonists of PC4 and potential antagonists of PC4 can be derived from the structure of the PACAP precursor and methods that reveal the interaction between the PACAP precursor and the PC4 enzyme. The structure of PACAP precursors for various species are recited in Hosoya, et al., Biochem. Biophys. Acta 1129:199 (1992) and Ogi, et al., Biochem. Biophys. Res. Comm. 173:1271 (1990). The biological activity of potential PC4 agonists can be determined (1) by measuring (e.g., by radioimmunoassay) the ability of the compound to stimulate the release, formation, or activity of PC4 or (2) by measuring the ability of the compound to form PACAP (e.g., by radioimmunoassy) from PACAP's precursor. The biological activity of potential PC4 antagonists can be determined (1) by measuring the ability of the compound to inhibit the formation of PACAP (e.g., by radioimmunoassay) from PACAP's precursor or (2) by measuring the ability of the compound to inhibit the release, formation, or activity of PC4.

Effect of PC4 on PACAP Precursor

GH4C1 cells (ATCC, Rockville, Md.) were stably transfected with the human PACAP precursor cDNA expression vector, pTS705 (Okazaki, et al., FEBS 298:49 (1992), and transiently co-transfected with PC4 cDNA expression vector, pCMV-PC4 (Dr. Kazuhisa Nakayama, University of Tsukuba, Tsukuba, Japan). After three days incubation, the cells were harvested and extracted with acetic acid. The extracts were fractionated with Sep-Pak C18 column (Waters, Milford, Mass.), and eluted with 40% acetonitrile/0.1% trifluoroacetic acid (TFA). The extracts were concentrated using speed vac concentrator and analyzed by reverse phase high performance liquid chromatography (HPLC). Each fraction was assayed for PACAP immunoreactivity by immunoassay using different antisera which recognize all PACAP-related peptides, PACAP-38, PACAP-24-38, or shorter fragments (Arimura, et al., Endocrinology 129:2787 (1991)).

The membrane fraction of GH4C1 cells was also analyzed by Western blot analysis using antisera which recognize PACAP and PACAP-related peptides. The results of reverse phase HPLC and Western blot analysis indicated that the extracts of GH4C1 cells transfected only by PACAP precursor expression vector contained the precursor of PACAP, while the extracts of cells co-transfected with PC4 expression vector also contained a considerable amount of PACAP-38 and a small amount of PACAP-27. The results indicate that PACAP precursor is a substrate for PC4, and PC4 yields matured PACAP-38 from PACAP's precursor.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of promoting spermatogenesis, said method comprising administering to a male in need thereof an effective amount of PACAP, a PACAP agonist, PC4, or a PC4 agonist.

2. A method of claim 1, wherein said method comprises the administration of an effective amount of PACAP or a PACAP agonist.

3. A method of claim 2, wherein said method comprises the administration of an effective amount of PACAP-38.

4. A method of claim 1, wherein said method comprises the administration of an effective amount of PC4 or a PC4 agonist.

5. A method of claim 1, said method comprising the administration of an effective amount of both (1) PACAP or a PACAP agonist and (2) PC4 or a PC4 agonist.

6. A method of inhibiting spermatogenesis, said method comprising administering to a male in need thereof an effective amount of a PC4 inhibitor.

7. A method of claim 1, wherein said method is administered locally.

8. A method of claim 1, wherein said method is administered systemically.

9. A method of claim 3, wherein said method is administered locally.

10. A method of claim 3, wherein said method is administered systemically.

11. A method of claim 6, wherein said method is administered locally.

12. A method of claim 6, wherein said method is administered systemically.

* * * * *